United States Patent
Shen et al.

(10) Patent No.: US 11,534,435 B2
(45) Date of Patent: Dec. 27, 2022

(54) DRUG CARRIER AND PREPARATION METHOD THEREOF

(71) Applicant: HAINAN POLY PHARM CO., LTD., Hainan (CN)

(72) Inventors: Youqing Shen, Hangzhou (CN); Quan Zhou, Hangzhou (CN); Changhuo Xu, Hangzhou (CN); Jiajia Xiang, Hangzhou (CN)

(73) Assignee: Hainan Poly Pharm Co., Ltd., Hainan (CN)

( * ) Notice: Subject to any disclaimer, the term of this patent is extended or adjusted under 35 U.S.C. 154(b) by 0 days.

(21) Appl. No.: 17/662,351

(22) Filed: May 6, 2022

(65) Prior Publication Data

US 2022/0257589 A1    Aug. 18, 2022

Related U.S. Application Data

(62) Division of application No. 16/642,010, filed as application No. PCT/CN2018/106827 on Sep. 21, 2018, now Pat. No. 11,364,232.

(30) Foreign Application Priority Data

Sep. 30, 2017    (CN) .......................... 201710917814.5

(51) Int. Cl.
| | |
|---|---|
| *A61K 47/58* | (2017.01) |
| *A61K 31/4745* | (2006.01) |
| *C08F 220/60* | (2006.01) |
| *C08F 220/36* | (2006.01) |
| *C08F 297/00* | (2006.01) |

(52) U.S. Cl.
CPC .......... *A61K 31/4745* (2013.01); *A61K 47/58* (2017.08); *C08F 220/365* (2020.02); *C08F 220/606* (2020.02); *C08F 297/00* (2013.01)

(58) Field of Classification Search
CPC .... A61K 47/58; A61K 31/4745; A61K 47/32; C08F 220/606; C08F 220/365; C08F 297/00; C08F 220/38; C08F 220/60; C08F 220/36; C08F 220/603; A61P 35/00
See application file for complete search history.

(56) References Cited

FOREIGN PATENT DOCUMENTS

| CN | 104829794 A | 8/2015 |
|---|---|---|
| CN | 104892870 A | 9/2015 |
| CN | 106146834 A | 11/2016 |
| CN | 106687142 A | 5/2017 |
| CN | 107033305   | * 8/2017 |
| CN | 107157928 A | 9/2017 |
| CN | 107519497 A | 12/2017 |
| CN | 109010838 A | 12/2018 |

OTHER PUBLICATIONS

Translation of CN 107033305 (Year: 2017).*
Huang, ACS Appl. Mater. Interfacess 2016, 8, 11226-11236 (Year: 2016).*
Wang, ACS NANO, vol. 9, No. 7, p. 7195-7206 (2015) (Year: 2015).*
Qiu, ACS Appl. Mater. Interfaces 2017, 9, 40887-40897 (Year: 2017).*
U.S. Appl. No. 16/642,010, filed Feb. 25, 2020, 2020/0215197, unknown.
Miura et al., *A Multilayered Cell Culture Model for Transport Study in Solid Tumors: Evaluation of Tissue Penetration of Polyethyleneimine Based Cationic Micelles*, Nano Today, vol. 9, No. 6, pp. 695-704 (2014).
Scott et al., *A phase II study of pegylated-camptothecin (pegamotecan) in the treatment of locally advanced and metastatic gastric and gastro-oesophageal junction adenocarcinoma*, Cancer Chemother Pharmacol, vol. 63, pp. 363-370 (2009).
Du et al., *A Tumor-Acidity-Activated Charge-Conversional Nanogel as an Intelligent Vehicle for Promoted Tumoral-Cell Uptake and Drug Delivery*, Angewandte Chemie Int. Ed., vol. 49, pp. 3621-3626 (2010).
Liu et al., *Amino Acid-Based Zwitterionic Polymer Surfaces Highly Resist Long-Term Bacterial Adhesion*, ACS Publications, Langmuir, vol. 32, pp. 7866-7874 (2016).
Chen et al., *Poly($N^5$-benzyl-L-glutamine)-Coated Silica Gels as Chiral Stationary Phase for Direct Resolution of Hydantoins*, Journal of Applied Polymer Science, vol. 49, 851-861 (1993).
Urano et al., *Rapid Cancer Detection by Topically Spraying a γ-Glutamyltranspeptidase—Activated Fluorescent Probe*, Science Translated Medicine, vol. 3, No. 110, p. 1-12 (2011).
Pelaz et al., *Surface Functionalization of Nanoparticles with Polyethylene Glycol: Effects on Protein Adsorption and Cellular Uptake*, American Chemical Society, NANO, vol. 9, No. 7, pp. 6996-7008 (2015).

(Continued)

*Primary Examiner* — Robert C Boyle
(74) *Attorney, Agent, or Firm* — Alston & Bird LLP

(57) ABSTRACT

This present invention relates to a drug carrier comprising a polymer of γ-glutamyl transpeptidase catalyzing hydrolysis-induced charge reversal, and a method for preparing the same. It can have a long circulation time in the blood, and can realize a charge reversal from negatively charged or the neutral to positively charged around the tumor blood vessel region, so that the positively charged polymer effectively penetrates deep into the tumor tissue, fast entering into the tumor cells, and greatly improves the therapeutic effect of the drug on the tumor. This overcomes the problems of slow diffusion of traditional polymer drug carriers in tumors and weak interaction with tumor cells, and has great significance in the field of anticancer treatment in the medical field.

2 Claims, 8 Drawing Sheets

(56) References Cited

OTHER PUBLICATIONS

Xu et al., *Targeted Charge-Reversal Nanoparticles for Nuclear Drug Delivery*, Angewandle Chemie Int. Ed., vol. 46, pp. 4999-5002 (2007).
Wang et al., *The Role of Micelle Size in Tumor Accumulation, Penetration, and Treatment*, American Chemical Society, NANO, vol. 9, No. 7, pp. 7195-7206 (2015).
Castellano et al., *γ-Glutamyltranspeptidases: sequence, structure, biochemical properties, and biotechnological applications*, Cellular and Molecular Life Sciences, vol. 69, pp. 3381-3394(2012).

\* cited by examiner

DRUG CARRIER AND PREPARATION METHOD THEREOF

CROSS-REFERENCE TO RELATED APPLICATION

This application is a divisional of U.S. patent application Ser. No. 16/642,010, filed Feb. 25, 2020, which is a 371 of international application of PCT application serial no. PCT/CN2018/106827, filed on Sep. 21, 2018, which claims the priority benefit of China application no. 201710917814.5, filed on Sep. 30, 2017. The entirety of each of the above-mentioned patent application is hereby incorporated by reference herein and made a part of this specification.

BACKGROUND OF THE INVENTION

1. Technical Field

The present invention belongs to the field of medical technology. Particularly, the present invention relates to the polymer of a γ-glutamyl transpeptidase catalyzing hydrolysis-induced charge reversal and its application in the field of drug delivery.

2. Background Art

"2016 China Cancer Registry Annual Report" shows that 6 people are diagnosed as malignant tumors per minute in 2016. Cancer incidence and mortality are on the rise. Cancer has become the number one cause of death for urban and rural residents in China. Up to now, chemotherapy based on the cytotoxic small molecular drugs still plays dominant role in cancer therapy. However, its high cytotoxin induced side effects and low therapeutic efficacy remain to be a formidable challenge.

Utilizing the Enhanced Permeability and Retention (EPR effect) of the tumor site, the polymer carrier can increase the anticancer drug's ability to accumulate in the tumor site and reduce the toxic and side effects of the drug. Existing preparations are in clinical application. However, at present these carriers can only reduce the systemic toxicity of the drug and fail to significantly improve the efficacy of the drug. Therefore, further designing the carrier to improve the therapeutic effect of the loaded drug is an urgent problem in the field of drug delivery.

The polymer carrier carries the drug to reach the tumor to exert its curative effect. It needs a circulation time in the blood that is long enough to flow through the tumor tissue and be enriched there, and then penetrates deep into the tumor and efficiently enters the cell to release the carried drug. Drug delivery vehicles such as traditional polyethylene glycol (PEG) and water-soluble polymers, such as drug-binding compounds, and micelles formed by amphiphilic polymers, can effectively avoid the immune system's elimination, so that drugs have longer blood circulation time. Some PEG-modified drugs have also entered clinical trials, such as PEG-modified camptothecin for the treatment of locally advanced and metastatic gastric cancer and adenocarcinoma at the junction of the gastroesophagus has entered clinical phase II (Scott L C, Yao J C, III ABB, et al. A phase-II study of pegylated-camptothecin (pegamotecan) in the treatment of locally advanced and metastatic gastric and gastro-oesophageal junction adenocarcinoma; Cancer Chemother Pharmacol 2009; 63:363-70).

However, drug carriers based on PEG water-soluble polymers have disadvantages. First, their ability to spread in tumors is weak (B. Pelaz, P. del Pino, P. Maffre, R. Hartmann, M. Gallego, S. Rivera-Fernandez, J. M. de la Fuente, G. U. Nienhaus, W. J. Parak, ACS Nano 2015, 9, 6996-7008.). Therefore, after being enriched in the tumor, they stay around the tumor capillaries and cannot spread to the depth of the tumor tissue, and cannot deliver drugs to tumor cells far away from the blood vessels. Second, the interaction of the carrier and tumor cells is very weak, which causes ingestion inefficiency of these drug-loading systems. When the drug concentration in the cells is too low, it greatly limits the effectiveness of the drug. Studies have found that a small amount of positive charges on the carrier can promote the penetration of the drug-loaded system into the tumor and uptake by tumor cells (Miura, S., Suzuki, H. & Bae, Y. H. *Nano Today* 9, 695-704 (2014)), but they cause fast elimination of the carrier from blood by the immune system. Utilizing the concept of charge reversal (P. Xu, E. A. Van Kirk, Y Zhan, W. J. Murdoch, M. Radosz, Y. Shen, *Angewandte Chemie-International Edition* 2007, 46, 4999-5002; J. Z. Du, T. M. Sun, W. J. Song, J. Wu, J. Wang, *Angewandte Chemie International Edition* 2010, 49, 3621-3626.), a drug delivery carrier that is neutral or slightly negatively charged in the blood can be transformed positively charged when it enters the acidic environment of the tumor tissue, so that it can be quickly taken up by tumor cells, ingest and exert better therapeutic effect. However, the acidic microenvironment in tumor tissue is generally far from the tumor capillaries and in a hypoxia region, and the size of the drug delivery carrier is much larger than small molecules (generally the carrier is tens of nanometers in diameter, and small molecule compounds are only a few nanometers). As a result, the carrier is difficult to diffuse and reach these slightly acidic areas to achieve charge reversal.

Therefore, it is urgently needed to develop such a drug carrier that has a long circulation time in the blood, and can change the charge from negative or neutral to positive around the tumor capillary so that the positively charged polymer penetrates deep into the tumor tissue, quickly enters the tumor cells, and greatly improves the therapeutic effect of the drug on the tumor.

Many human tumors including colon, liver, and ovarian adenocarcinoma, particularly the active cells in the periphery of blood vessels, overexpress GGT, which is an intrinsic membrane enzyme mainly expressed on the external surface of metabolically active tumor cells at the periphery of tumor tissue of blood vessels (Castellano, I. & Merlino, A. γ-Glutamyltranspeptidases: Sequence, structure, biochemical properties, and biotechnological applications, *Cell. Mol. Life Sci,* 2012, 69, 3381-3394). It cleaves various γ-glutamylamides and thus has been used for tumor-specific activation of fluorescent probes, prodrugs and multifunctional nanocarriers (Urano, Y. et al. Rapid cancer detection by topically spraying a γ-glutamyltranspeptidase-activated fluorescent probe, *Sci. Transl. Med,* 2011, 3, 110ra119).

SUMMARY OF THE INVENTION

The present invention provides a polymer of γ-glutamyl transpeptidase (GGT) catalyzing hydrolysis-induced charge reversal, which can be used as a drug carrier to deliver the anticancer drug. The polymer is neutral but can be hydrolyzed under the catalysis of highly expressed γ-glutamyl transpeptidase to generate amino groups, which carry positively charges, so as to trigger fast penetration in the tumor and fast uptake by the tumor cells. This overcomes the issues of slow diffusion in the tumor and slow uptake by the tumor cells of traditional polymer drug carriers.

A polymer of γ-glutamyl transpeptidase catalyzing hydrolysis-induced charge reversal, the polymer comprising γ-glutamyl transpeptidase responsive element, the element is represented by Formula (I):

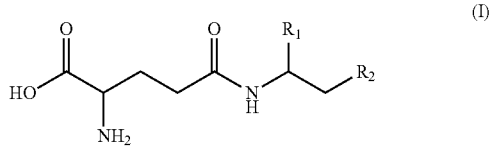

Wherein, $R_1$ is any one of a hydrogen, an alkyl group, an aryl group, or a halogen; $R_2$ is any one of a hydrogen, an alkyl group, a carbonyl group, an aryl group, or a halogen.

The present invention also provides the preparation method of the polymer of γ-glutamyl transpeptidase catalyzing hydrolysis-induced charge reversal, which can be obtained by direct polymerization of a monomer containing the γ-glutamyl transpeptidase responsive element.

The monomer containing the γ-glutamyl transpeptidase responsive element is composed of a γ-glutamyl transpeptidase responsive element moiety and a polymerizable functional group. The structure of the monomer is represented by Formula (II):

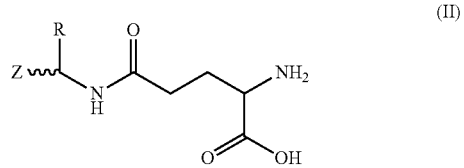

Wherein Z represents the polymerizable function group; R is any one of a hydrogen, an alkyl group, an aryl group or a halogen.

The monomer containing the γ-glutamyl transpeptidase responsive element comprises an acrylamide-based monomer containing the γ-glutamyl transpeptidase responsive element, an acrylate-based monomer containing the γ-glutamyl transpeptidase responsive element, a methacrylamide-based monomer containing the γ-glutamyl transpeptidase responsive element, or a methacrylate-based monomer containing the γ-glutamyl transpeptidase responsive element.

The polymer of γ-glutamyl transpeptidase catalyzing hydrolysis-induced charge reversal can be prepared by the existing polymerization method using the monomer containing the γ-glutamyl transpeptidase responsive element.

The present invention also provides a method for preparing of a drug carrier prepared by the polymer of γ-glutamyl transpeptidase catalyzing hydrolysis-induced charge reversal, comprising: the drug carrier is synthesized by existing polymerization method of random copolymerization or block copolymerization between the monomer containing the γ-glutamyl transpeptidase responsive element and the monomer of the loaded drug.

The drug carrier prepared by the polymer of γ-glutamyl transpeptidase catalyzing hydrolysis-induced charge reversal, comprising a structure represented by Formula (III) or Formula (IV):

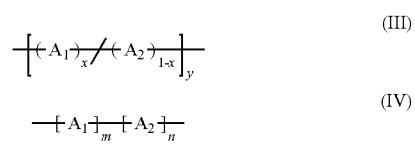

where $A_1$ is the monomer containing the γ-glutamyl transpeptidase responsive element, $A_2$ is a monomer of a loaded drug; Formula (III) represents a structural formula of a random copolymer formed by $A_1$ and $A_2$, wherein x is the mole ratio of monomer $A_1$, y is the degree of polymerization, x=0.01-0.99, y=3-300; Formula (IV) represents a structural formula of a block copolymer formed by $A_1$ and $A_2$, wherein m and n are the numbers of repeating units, m=3-300, n=1-500.

The loaded drug is anticancer drugs, including doxorubicin, camptothecin, camptothecin derivatives, paclitaxel, platinum-based drugs, irinotecan, methotrexate, sophocarpidine, salvianolic acid, or protein, polypeptides, DNA molecules, or RNA molecules.

An example of the acrylamide-based monomer containing the γ-glutamyl transpeptidase responsive element, GABEAM, GABEA, is represented by the structural formulae as follows:

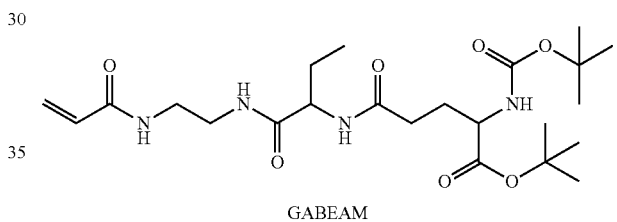

GABEAM

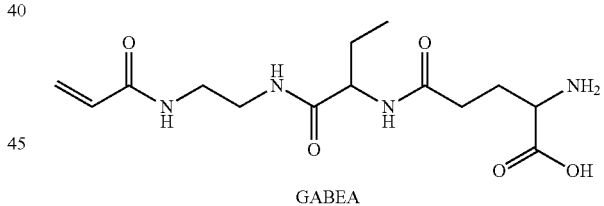

GABEA

The drug carrier of the polymer of γ-glutamyl transpeptidase catalyzing hydrolysis-induced charge reversal is prepared by existing polymerization method using the acrylamide-based monomer containing the γ-glutamyl transpeptidase responsive element and the monomer of the loaded drug.

For example, the acrylamide-based monomer containing the γ-glutamyl transpeptidase responsive element GABEAM, and the monomer of the loaded anticancer drug camptothecin (CPT) of the methacrylate-based monomer CPTM was subjected to random copolymerization, followed by deprotection by trifluoroacetic acid (TFA), to obtain the drug carrier of the polymer of γ-glutamyl transpeptidase catalyzing hydrolysis-induced charge reversal: PGABEA-CPT, its composition can be controlled by the ratio of two monomers, and the structural formula is as shown in Formula (IIIa):

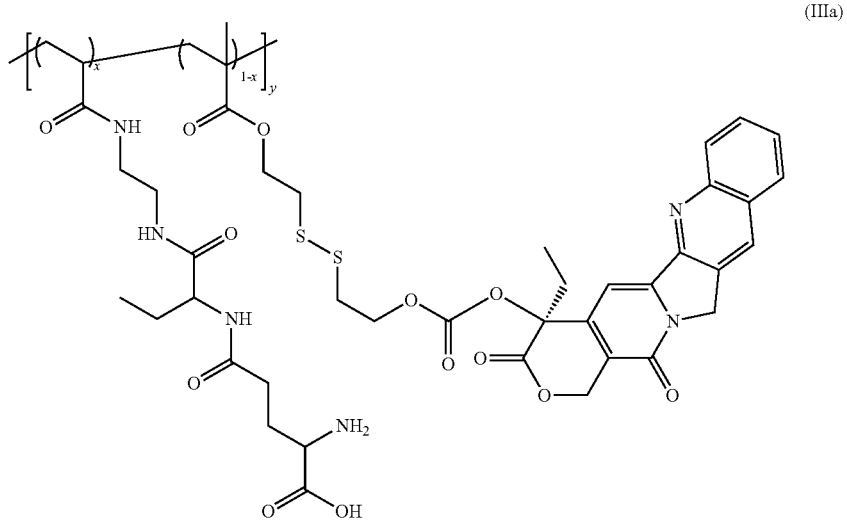

(IIIa)

Wherein, x=0.01-0.99; y=3-300.

An example of the methacrylate-based monomer containing the γ-glutamyl transpeptidase responsive element, GABEMAM, GABEMA, is represented by the structural formulae as follows,

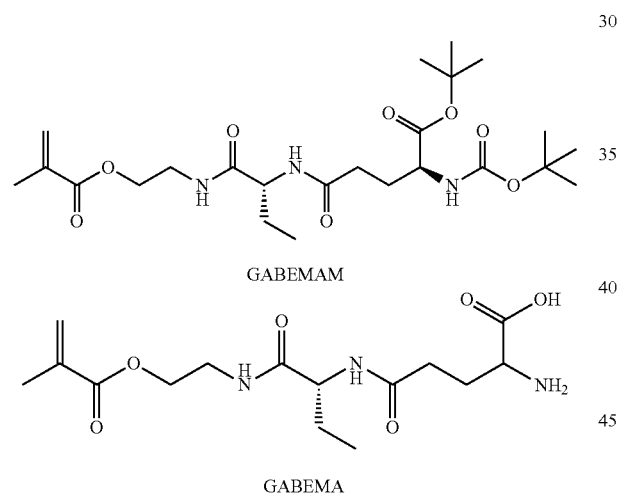

GABEMAM

GABEMA

The drug carrier of the polymer of γ-glutamyl transpeptidase catalyzing hydrolysis-induced charge reversal is prepared by existing polymerization method using the methacrylate-based monomer containing the γ-glutamyl transpeptidase responsive element and the monomer of the loaded drug.

For example, the methacrylate-based monomer containing the γ-glutamyl transpeptidase responsive element, GABEMAM and the loaded anticancer drug 7-ethyl-10-hydroxycamptothecin (SN38) of the methacrylate-based monomer HEMASN38 was subjected to block copolymerization, followed by deprotection with trifluoroacetic acid (TFA), to obtain the drug carrier of the polymer of γ-glutamyl transpeptidase catalyzing hydrolysis-induced charge reversal: PHEMASN38-PGABEMA, the number of average polymerization degree m, n is controlled by the amount of two monomers, the structural formula is represented by Formula (IVa) as follows:

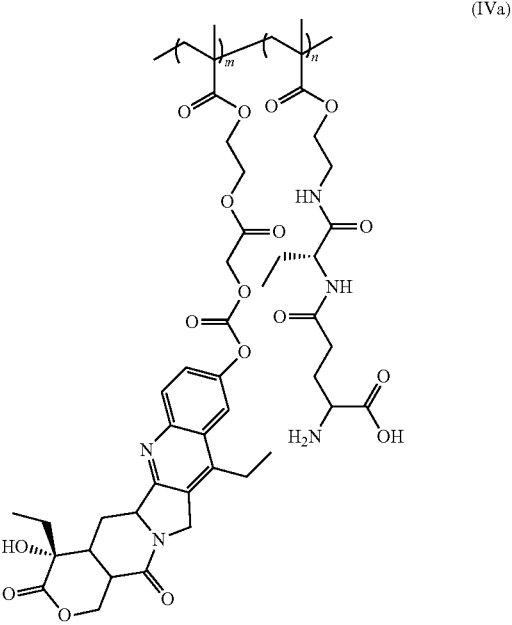

(IVa)

Wherein, m=3-300, n=3-300.

The mechanism of the drug carrier of the polymer of γ-glutamyl transpeptidase catalyzing hydrolysis-induced charge reversal for antitumor therapy is: in the vicinity of tumor capillaries, tumor cells are actively grown and γ-glutamyl transpeptidase is highly expressed. After extruding the tumor capillaries, the drug carrier is hydrolyzed to lose γ-glutamates under the action of γ-glutamyl transpeptidase to generate amino groups, and achieving positively charged, which enables efficient penetration of loaded drug in the tumor and fast entry into the cells to exert the drug efficacy.

Further, the γ-glutamyl transpeptidase responsive element of the present invention is an ion pair, which makes the drug carrier hydrophilic and electrically neutral. Thus, in the blood circulation system, it has similar water solubility, biocompatibility, and long blood circulation time as the PEG-based drug carrier, thereby, it has a high tumor accumulation capacity.

Compared with the existing technology, the present invention has the following beneficial effects:

(1) Experimental results in mice show that: compared with traditional drug carriers such as PEG that cannot achieve charge reversal, the charge reversal carrier synthesized by the present invention can quickly achieve positive charge reversal under the specific action of γ-glutamyl transpeptidase on the cancer cell surface, and thus the rate of entering the cancer cell is greatly improved. It overcomes the shortcomings of slow entering rate of similar carriers, greatly increases the concentration of anti-tumor drugs in the cells, and improves the utilization rate of the drugs in the tumor cells.

(2) Compared with the acidic catalytic charge reversal drug carriers, whose charge reversal can occur only in the acidic microenvironment of tumors far away from blood capillaries, the carrier of the present invention can achieve charge reversal on the tumor surface in the vicinity of the blood capillaries. This rapid charge reversal allows the polymer to diffuse efficiently into the tumor and quickly taken up by tumor cells.

(3) The polymer of γ-glutamyl transpeptidase catalyzing hydrolysis-induced charge reversal provided by the present invention is sensitive, efficient and specific to the γ-glutamyl transpeptidase. The polymer carrier can be dissolved in water to form a solution, an emulsion, nanometer-sized micelles or vesicles. The required solution dispersion form can be obtained by the preparation methods commonly used in the art, which is easy to implement.

(4) The synthesized polymer of γ-glutamyl transpeptidase catalyzing hydrolysis-induced charge reversal provided by the present invention has good water solubility and biocompatibility as a drug carrier, and its performance in this aspect is similar to that made by the gold standard PEG in the field. The drug carrier is equivalent, and can be circulated in the body for a long time, so it is easy to be concentrated in tumor areas with irregular blood vessels, which reduces the accumulation of drugs in normal tissues, reduces the toxic and side effects of drugs on normal tissues, and improves biocompatibility. At the same time, it can significantly improve the pharmaceutical effect of the drug.

The invention proposes for the first time to use an enzyme-catalyzed charge reversal polymer as an anti-tumor drug carrier, and provides a new carrier for the delivery of anticancer drugs: it can have a long circulation time in the blood, and can realize a charge reversal from negatively charged or the neutral to positively charged around the blood vessel region, so that the positively charged polymer effectively penetrates deep into the tumor tissue, fast entering into the tumor cells, greatly improves the therapeutic effect of the drug on the tumor, and has great significance in the field of anticancer treatment in the medical field.

Further, when the charge reversal drug carrier of the polymer of γ-glutamyl transpeptidase catalyzing hydrolysis-induced charge reversal of the present invention is provided, if the drug carrier is chemically linked, then the drug carrier will have the function of treating disease, preventing disease, carrying a therapeutic gene, or tracing the lesion site at the same time, that is, the polymer is a potential molecular precursor that has the function of treating disease, preventing a disease, carrying a therapeutic gene or tracing the lesion site.

DETAILED DESCRIPTION OF THE EMBODIMENTS

Figure 1:
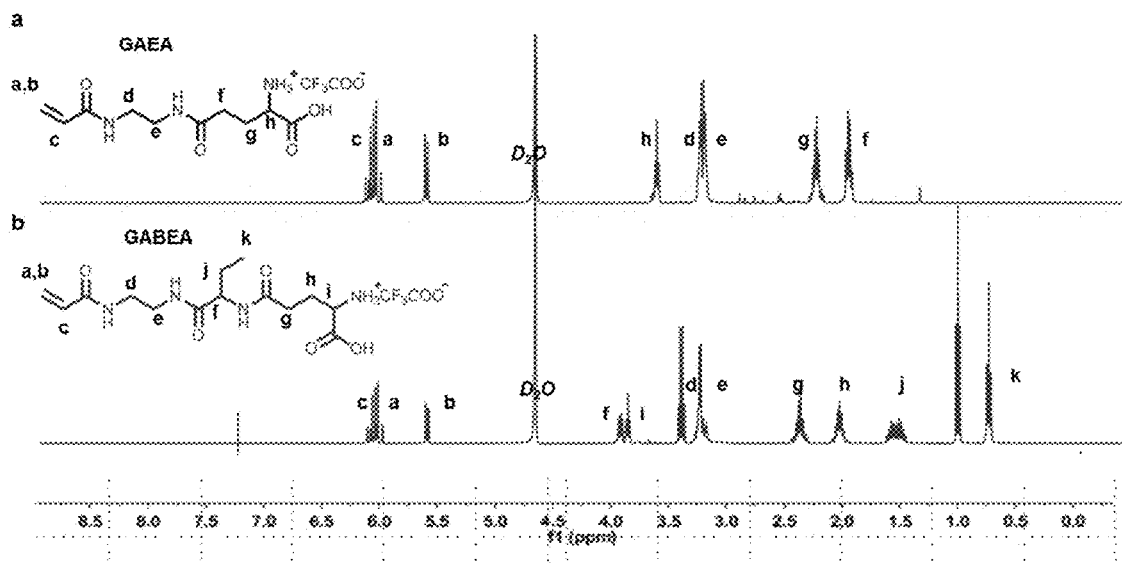
FIG. 1 shows the $^1$H-NMR spectra of γ-glutamyl transpeptidase-responsive monomer GABEA and control monomer GAEA as prepared in Example 1.

To further understand the present invention, method for preparing the polymer of γ-glutamyl transpeptidase catalyzing hydrolysis-induced charge reversal and its application method in the field of drug delivery are specifically described in combination with the following examples. However, the present invention is not limited by these specific embodiments or application examples. Changes, substitution, and simplified combination performed by those skilled in the art under the core guiding principles of the present invention are all included in the protection scope of the present invention.

Example 1: Synthesis of γ-Glutamyl Transpeptidase-Response Monomer GABEA and Control Monomer GAEA 1) Dissolve 5.05 mL of ethanediamine in 75 mL of water, and the pH of the ethanediamine-containing solution was adjusted to 8.5 with 3M hydrochloric acid. 6.7 mL of acryloyl chloride dissolved in 50 mL of chloroform was added dropwise to the above solution. The mixture was reacted under room temperature for 2 h. After the aqueous and organic phase was separated with separation funnel, the aqueous layer was washed with chloroform for three times, concentrated under spin vacuum to obtain a white solid 1. The white solid was then washed with methanol repeatedly. The filtrate was concentrated to obtain as a clear yellow solution and stored in refrigerator.

2) Dissolve 2 g of Boc-Glu-OtBu (0.3 g, 0.9 mmol) in 50 mL of anhydrous dichloromethane, and added in batches to

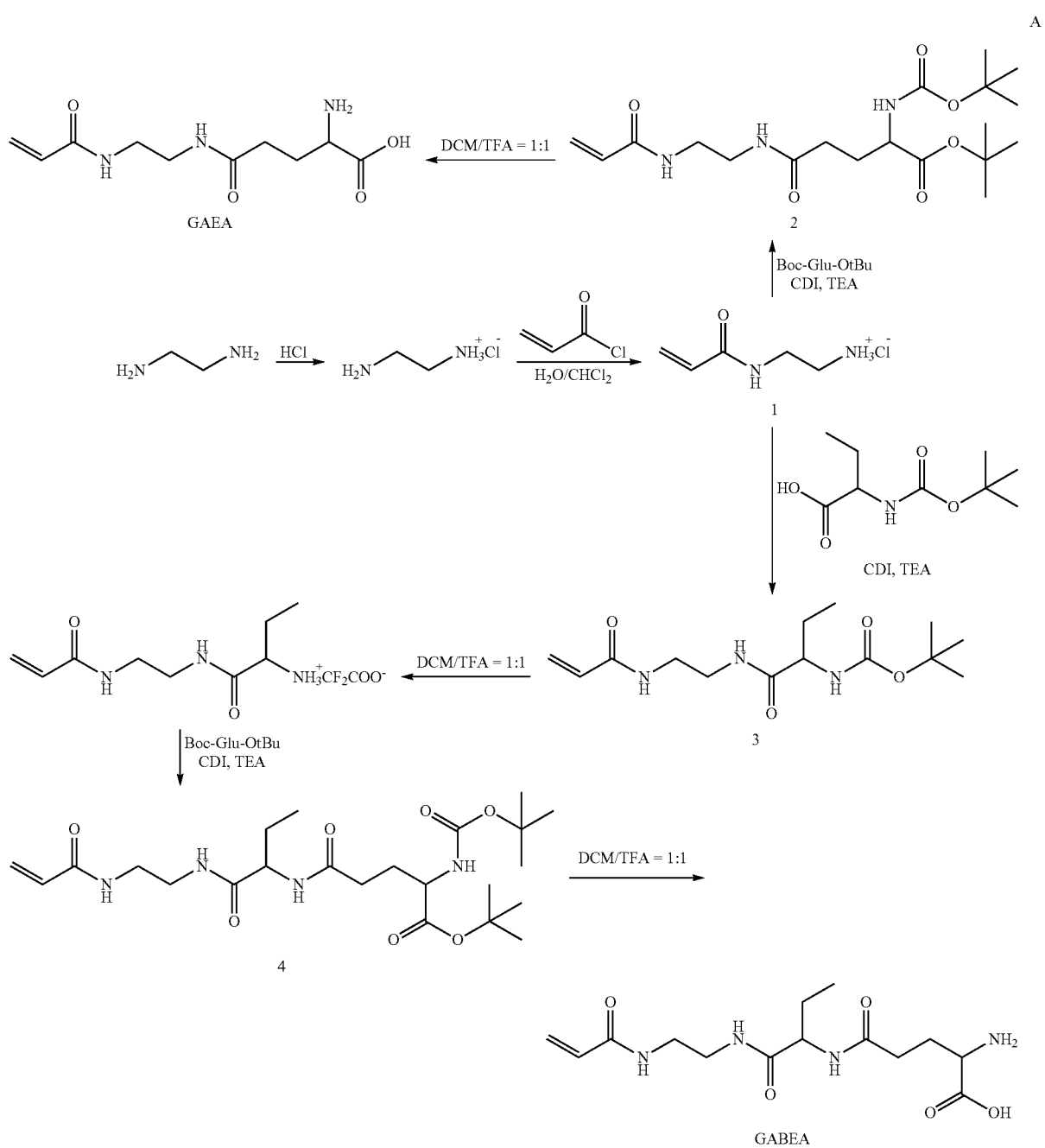

N,N'-carbonyldiimidazole (1.78 g), stirred to react under room temperature for 2 h. After the reaction, 3.5 mL of triethylamine was added to the 2.08 g of the yellow solution prepared above, and stirred at room temperature for overnight; the solution was successively washed with 1 M hydrochloric acid solution for three times, and washed with saturated NaHCO₃ solution and saturated NaCl solution. After dried over anhydrous magnesium sulfate, white solid 3 was obtained.

3) The obtained product 3 (1.5 g, 5 mmol) was dissolved in 4 mL of dichloromethane, deprotection by adding an equal volume of trifluoroacetic acid at room temperature for 6 h. After drying, entrained twice with dichloromethane, and then placed in vacuum to dry for 4 h to use. Dissolve Boc-Glu-OtBu (1.44 g, 4.75 mmol) in 50 mL of anhydrous dichloromethane, and added in batches to N,N'-carbonyldiimidazole (0.92 g, 5.7 mmol), react under room temperature for 2 h. 2 mL of triethylamine was added to the reacting solution above, slowly adding the deprotected trifluoroacetate dropwise, and stirred at room temperature for overnight. The solution was successively washed with 1 M hydrochloric acid solution for three times, and washed with saturated NaHCO₃ solution and saturated NaCl solution, and spin to dry. Finally, use ethyl acetate:methanol=10:1 as developing agent to pass through a silica gel column to obtain a while solid 4.

4) The obtained product 4 above was dissolved appropriate amount of dichloromethane, adding an equal volume of trifluoroacetic acid dropwise, stirring overnight under room temperature for overnight, after spin dry, entrained with methanol for three times, and precipitate in ethanol to obtain the product GABEA.

5) Dissolve 0.30 g of Boc-Glu-OtBu in 20 mL of anhydrous dichloromethane and added in batches to N,N'-carbonyldiimidazole (0.18 g), stir to react under room temperature for 2 h. After the reaction, 0.35 mL of triethylamine was added to the N-2-(aminoethyl)-acrylamide hydrochloride prepared above, and stirred at room temperature for overnight. The solution was successively washed with 1 M hydrochloric acid solution for three times, and washed with saturated NaHCO₃ solution and saturated NaCl solution, respectively. The organic phase was dried over anhydrous magnesium sulfate, and the solvent was distilled of on a rotary evaporator. White solid 2 was obtained.

6) The obtained product 2 above was dissolved in appropriate amount of dichloromethane, an equal volume of trifluoroacetic acid was added dropwise and react at room temperature for overnight. After spin drying, entrained with methanol for three times, and precipitate in ethanol to obtain the product GAEA.

It can be known from the NMR spectra in FIG. 1 that GABEA monomer with higher purity and GAEA monomer as control were obtained.

Example 2. γ-Glutamyl Transpeptidase (GGT)-Catalyzed Hydrolysis of Small Molecules GABEA and GAEA

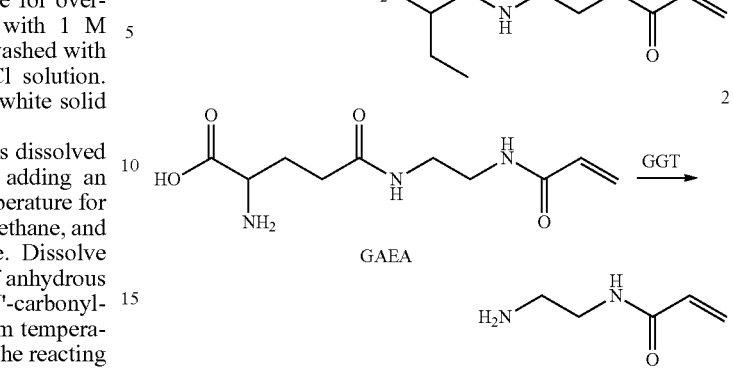

Dissolve monomers GABEA or GAEA in PBS solution (pH=7.4, prepared by D₂O) and configure the monomer concentration to 25 μM in the PBS solution. γ-glutamyl transpeptidase was added into the solution respectively so that the concentration of γ-glutamyl transpeptidase in the solution is 1 U/mL. At this time, the obtained product was immediately detected by nuclear magnetic resonance. The sample was placed in a 37° C. incubator and analyzed the nuclear magnetic resonance at different times.

Figure 2:
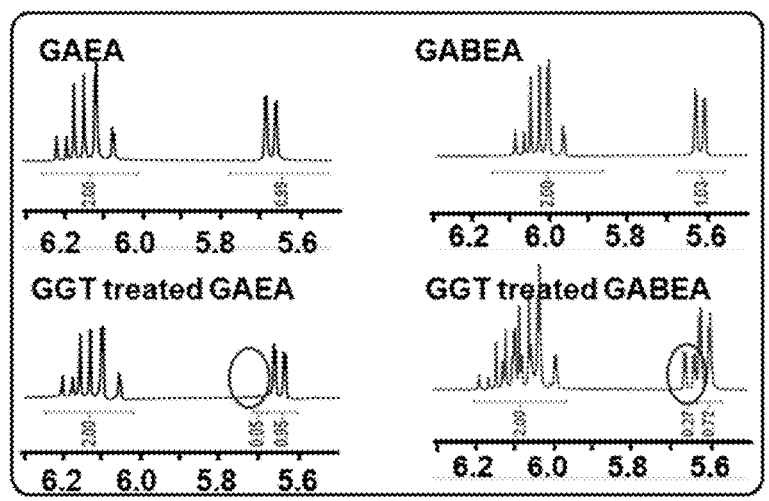
FIG. 2 illustrates the NMR changes of γ-glutamyl transpeptidase-responsive monomer GABEA and control monomer GAEA after the hydrolysis by γ-glutamyl transpeptidase as depicted in Example 2.

As depicted in FIG. 2, the hydrolysis activity of γ-glutamyl transpeptidase of GABEA is far greater than GAEA.

Example 3: Synthesis of γ-Glutamyl Transpeptidase-Responsive Polymer PGABEA-CPT and Control Polymer PGAEA-CPT Weigh 2,2'-dithiodiethanol (14.84 g), methacrylic anhydride (14.84 g), DMAP (1.2 g) in 12 mL of pyridine, stir at room temperature overnight, spin dry the pyridine, and redissolve in dichloromethane. It was washed three times with 1 M hydrochloric acid solution, then washed with saturated NaHCO₃ solution and saturated NaCl solution, dried and spin-dried, and finally passed through a silica gel column with ethyl acetate:n-hexane=1:3 as a developing agent to obtain a yellow liquid product (HSEMA).

CPT (2.0 g, 5.74 mmol) and 4-dimethylaminopyridine (DMAP) (2.11 g, 17.3 mmol) were suspended in 50 mL of dry dichloromethane, and triphosgene (0.567 g, 1.92 mmol) was added under the protection of argon. After stirring for 30 min at room temperature, the solution gradually cleared. Dissolve HSEMA (1.40 g, 6.31 mmol) in 15 mL of dry tetrahydrofuran, add the above solution dropwise, stir at room temperature overnight, spin dry to ¼ volume solution, add 50 mL of dichloromethane again, and use 1 M hydrochloric acid solution and the saturated NaCl solution to wash, dried over anhydrous MgSO₄ and spin-dried, and passed through the column with ethyl acetate to obtain CPTM as a yellow solid powder.

Weigh compound 2 (229 mg) or 4 (270 mg) synthesized in Example 1, CPTM (70 mg), AIBN (1 mg) dissolved in 1.5 mL DMF, nitrogen was bubbled to remove oxygen for 30 min, reacted at 80° C. for 12 h, and then dialysis through DMSO (250 mL×4), ethyl acetate (250 mL×2), remove the liquid from the dialysis bag, spin dry the solvent, redissolve in 4 mL of dichloromethane, add an equal volume of trifluoroacetic acid dropwise for deprotection, and react at room temperature for 12 h. After spin-drying the solvent, dialysis was performed three times with sodium phosphate buffer solution (pH=7.4), and then dialyzed with deionized water, and lyophilized to obtain the product.

Figure 3:
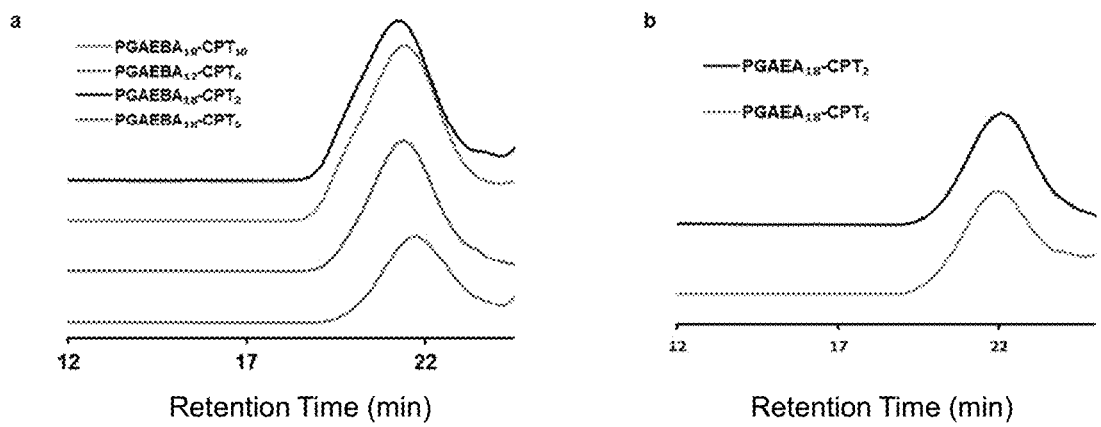
FIG. 3 shows gel permeation chromatography (GPC) of PGABEA-CPT and PGAEA-CPT prepared in Example 3, wherein a is GPC image of PGABEA-CPT, and b is GPC image of PGAEA-CPT.

It is shown in FIG. 3 that PGABEA-CPT and PGAEA-CPT polymers with uniform distribution and molecular weights around 10,000 before deprotection were obtained.

Example 4: Synthesis of Control Compound PEG-SS-CPT

CPT (0.7 g, 2 mmol) and DMAP (0.78 g) were suspended in 50 mL of dry dichloromethane, and triphosgene (0.22 g, 0.67 mmol) was added under the protection of argon. After stirring at room temperature for 30 min, the solution gradually cleared. Dissolved 2,2'-dithiodiethanol (1.54 g) in 20 mL of dry tetrahydrofuran and added to the above solution dropwise, stirred overnight at room temperature, spin-dried to ¼ volume solution, re-added 50 mL of dichloromethane, washed with 1 M hydrochloric acid solution and saturated NaCl solution, dried with anhydrous $MgSO_4$ and spin-dried, and passed through the column with ethyl acetate:methanol=10:1 to obtain CPT-SS-OH as a yellow solid powder.

Figure 4:
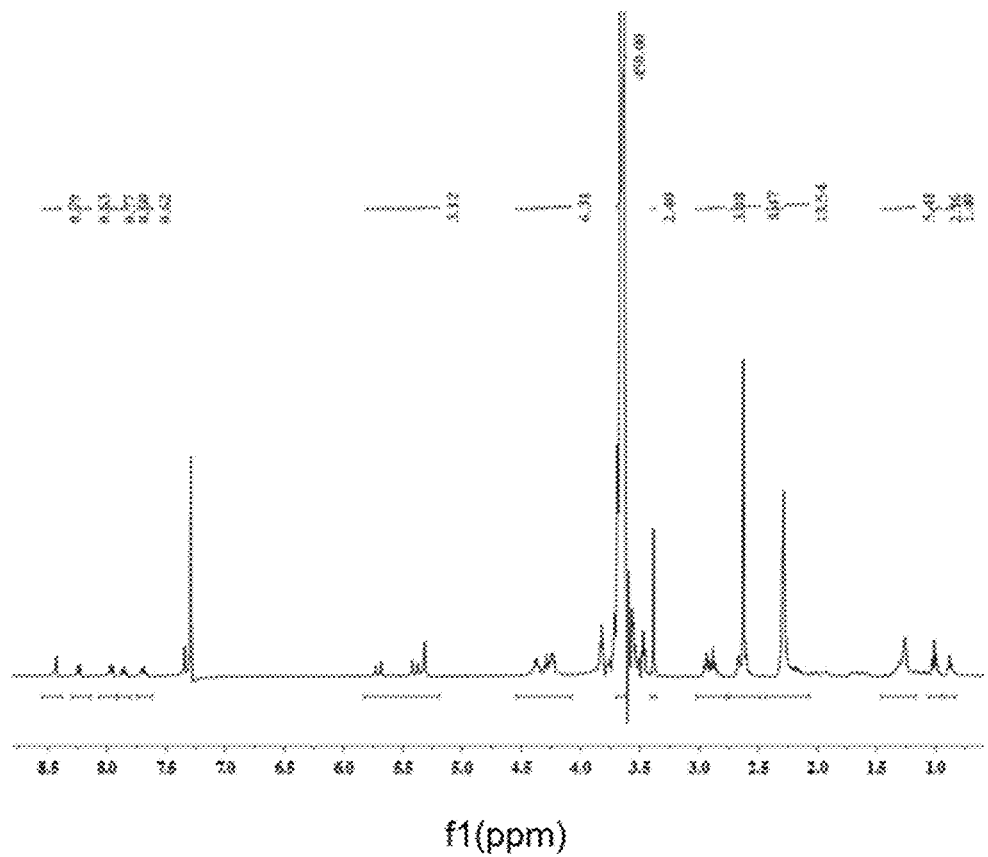
FIG. 4 shows the $^1$H-NMR spectrum of PEG-SS-CPT as prepared in Example 4.

Weigh $PEG_{5000}$-COOH (106 mg), CPT-SS-OH (16 mg), EDC.HCl (5.8 mg) and DMAP (5 mg) in 5 mL of dry dichloromethane, stir at for 48 h at room temperature, and then dissolved in 5 mL of DMSO, DMSO dialysis (250 mL×4), freeze-dried to obtain the product PEG-SS-CPT, and its NMR characterization is shown in FIG. 4.

Example 5: Fluorescence Labeling of the Synthesized PBGAEA$^{Cy5}$-CPT, PGAEA$^{Cy5}$-CPT and PGAEA$^{RhoB}$-CPT The PGAEA-CPT (20 mg) or PGABEA-CPT (20 mg) was dissolved in 1 mL of deionized water. Then, 0.2 mg of Cy$^5$-NHS or RhoB-NHS was added to the above solution, and the mixture was stirred overnight at room temperature. Finally, dialysis was performed with methanol and water to remove unreacted fluorescent molecules. After dialysis, lyophilization yielded product PGABEA$^{Cy5}$-CPT, PGAEA$^{Cy5}$-CPT and PGAEA$^{RhoB}$-CPT; the microplate reader is used to detect and quantify the modified Cy5 or RhoB fluorescence intensity.

Example 6: Experiment of γ-Glutamyl Transpeptidase-Catalyzed Charge Reversal of PGABEA-CPT Weigh 2 mg of polymer PGABEA-CPT or PGAEA-CPT in 1 mL HEPES buffer, add glutamate transpeptidase (10 U/mL), and incubate in a shaker (37° C., 200 r/min), after some specific time points, 20 μL of the sample solution was taken from 500 μL of HEPES buffer, the Zeta potential was measured, and the average from three measurement was taken.

Figure 5:
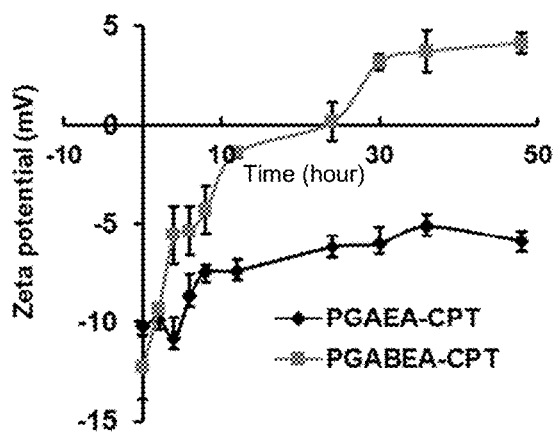
FIG. 5 shows the kinetics of zeta potential over time measured for the PGABEA-CPT and PGAEA-CPT polymers under reaction of γ-glutamyl transpeptidase in Example 6.

It can be seen from FIG. 5 that under GGT catalysis, the potential energy of PGABEA-CPT changes from negative to positive, while the potential of PGAEA-CPT has been kept negative due to the lower catalytic activity of GGT to GAEA.

Example 7 Synthesis of γ-Glutamyl Transpeptidase Responsive Block Polymer PHEMASN38-PGABEMA

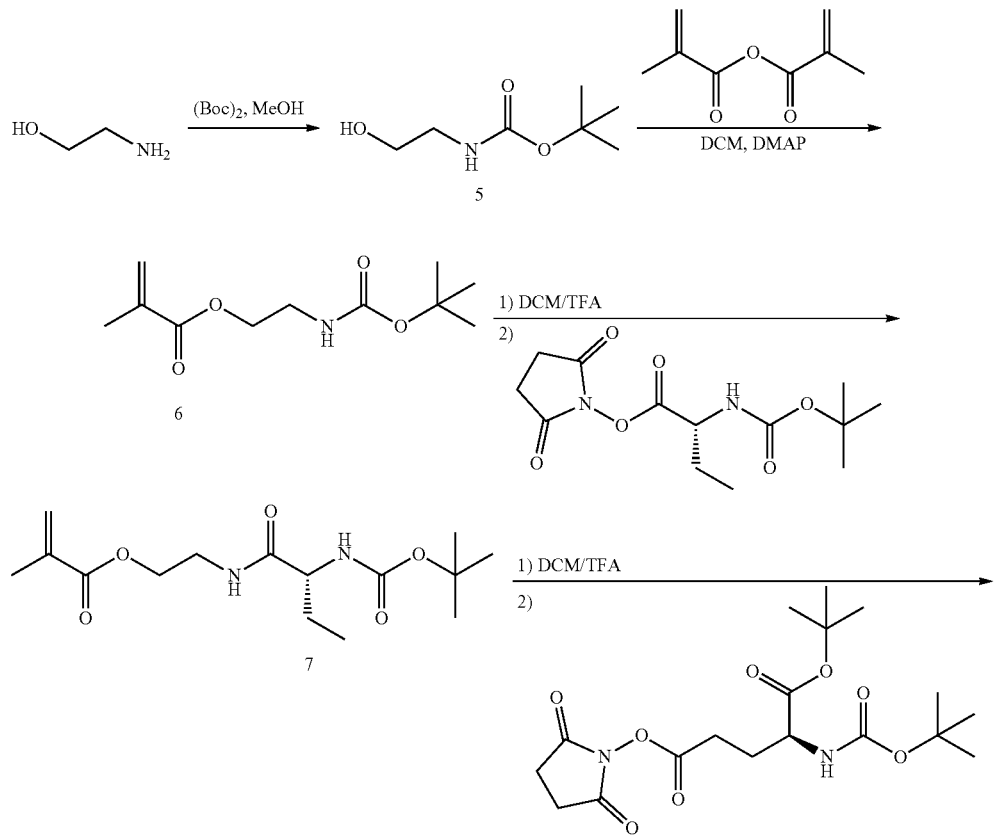

-continued

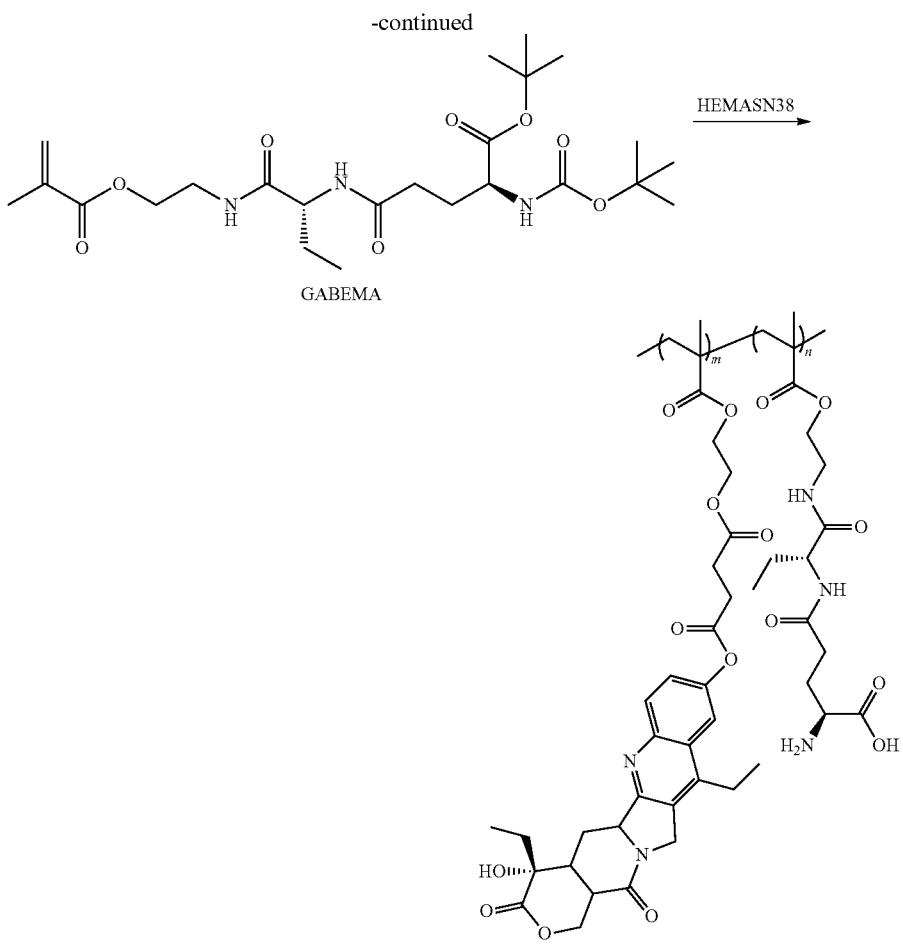

GABEMA

1) Ethanolamine (5 g) was dissolved in methanol (50 mL) and di-tert-butyl dicarbonate (18 g) was added dropwise under an ice bath. The reaction mixture was performed at room temperature for 2 h. After concentration by evaporation, 200 mL of ethyl acetate was added and the mixture was washed with saturated brine for three times, dried over anhydrous sodium sulfate and concentrated to obtain a colorless liquid 5 (Boc-2-ethanolamin).

2) Dissolve Boc-2-ethanolamine (5 g) and DMAP (4.2 g) in 100 mL of anhydrous dichloromethane, add methacrylic anhydride (5.2 g) dropwise in an ice bath, remove the ice bath, react at room temperature for 3 h, spin off tetrahydrofuran, add 200 mL of ethyl acetate, and washed three times each with 3% HCl, saturated sodium bicarbonate, and saturated brine, dried over anhydrous sodium sulfate, and spin-dried to obtain a white solid 6.

3) Dissolve Boc-L-2-aminobutyric acid (10 g), N-hydroxysuccinimide (NHS, 8.5 g) and DMAP (9.1 g) in 100 mL of dry dichloromethane, add dicyclohexylcarbodiimide (DCC, 15.2 g) in dichloromethane (40 mL) dropwise in an ice bath, remove the ice bath, react at room temperature overnight, filter to remove dicyclohexylurea (DCU), concentrate the filtrate, and to recrystallize Boc-L-2-aminobutyric acid-NHS ester as white crystals under ethyl acetate/n-hexane. Compound 6 (3.88 g) was dissolved in 10 mL of dichloromethane, and an equal volume of trifluoroacetic acid was added to deprotect it. The raw materials disappeared by TLC monitoring and concentrated. 20 mL of dichloromethane and 8 mL of triethylamine were added, and a solution of Boc-L-2-aminobutyric acid-NHS ester (4.4 g) in dichloromethane was added dropwise at room temperature, and the reaction was carried out for 3 hours, spin dry to remove dichloromethane. Add 100 mL of ethyl acetate, washed three times each with 3% HCl, saturated sodium bicarbonate, and saturated brine, dried over anhydrous sodium sulfate, and spin-dried to obtain a colorless viscous liquid 7.

4) Dissolve Boc-L-Glu-1-OtBu (10 g), NHS (5.7 g), and DMAP (1.5 g) in 100 mL of dry dichloromethane, and add DCC (10.2 g) which is dissolved in methylene chloride (30 mL), remove the ice bath, react at room temperature overnight, remove DCU by filtration, concentrate the filtrate, and recrystallize in ethyl acetate/n-hexane to obtain Boc-L-Glu-1-OtBu-NHS ester as white crystals. Compound 7 (4.5 g) was dissolved in 10 mL of dichloromethane, and an equal volume of trifluoroacetic acid was added for deprotection, the raw materials disappearance was monitored by TLC, concentrated, 30 mL of dichloromethane and 10 mL of triethylamine were added. Boc-L-Glu-1-OtBu-NHS ester (3.9 g) in dichloromethane solution is added dropwise under room temperature, react for 3 h, remove the dichloromethane, add 100 mL ethyl acetate, and wash each with 3% HCl, saturated sodium bicarbonate, saturated brine for three times, dried over anhydrous sodium sulfate, concentrated, and passed through a silica gel column with ethyl acetate: n-hexane=1:1 as a developing agent to obtain GABEMA as a white solid.

Figure 6:
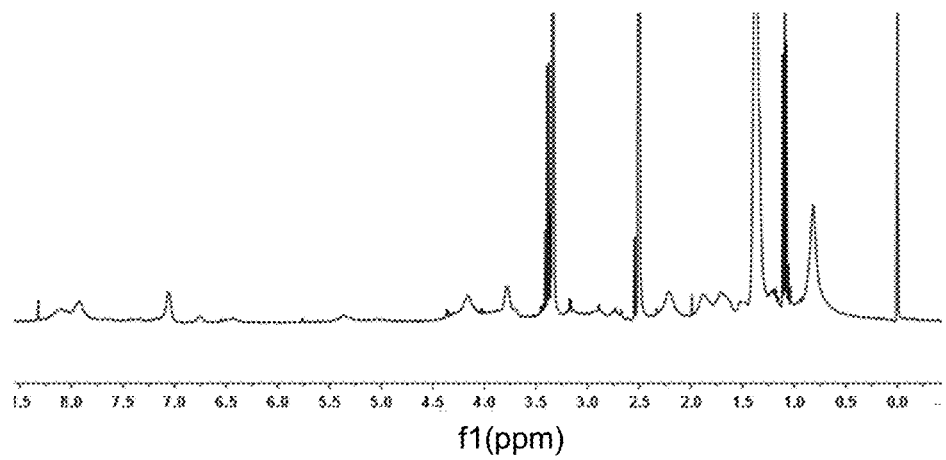
FIG. 6 shows the $^1$H-NMR spectra of PHEMASN38-PGABEMA prepared in Example 7.

5) HEMASN38 which was prepared according to the literature (Wang J, Mao W Lock L L, et al. *ACS nano*, 2015, 9(7): 7195-7206) (140 mg), ethyl 2-bromoisobutyrate (5.5 mg) and CuBr (4.0 mg) was added to a polymerization bottle, 2 mL of dried DMF was added, and after removal by freeze-thaw, pentamethyldiethylenetetramine (4.9 mg) was added, and polymerization was performed at 50° C. for 24 h. GABEMA (280 mg) was added into the mixture to continue the reaction for another 24 h. The resultant solution was dialyzed with DMSO (250 mL×4), dialyzed with ethyl acetate (250 mL×2), remove the liquid from the dialysis bag, spin dry the solvent, and re-dissolve in 4 mL of dichloromethane. An equal volume of trifluoroacetic acid was added dropwise for deprotection, and the reaction was carried out at room temperature for 12 hours. The solution was concentrated to 2 mL. A large amount of ether was added, filtered and washed with ether. Drying to obtain the light-yellow product PHEMASN38-PGABEMA, and its nuclear magnetic characteristics are shown in FIG. 6.

Application Example 1: Application of PGABEA-CPT Random Copolymer as Anticancer Drug (1) Preparation of PGABEA-CPT Injection Calculate the corresponding concentration according to the dose. Dissolve the PGABEA-CPT prepared in Example 3 in PBS or physiological saline buffer solution, ultrasonic shake to dissolve to prepare a homogeneous, clear and transparent injection solution. Store at −20° C. and avoid repeated freeze-thaw cycles.

The PGABEA-CPT solution prepared by the above method is taken as an example for detection and subsequent experiments, and the detection methods are those conventional methods in the art.

(2) Cytotoxicity Test

Figure 7:
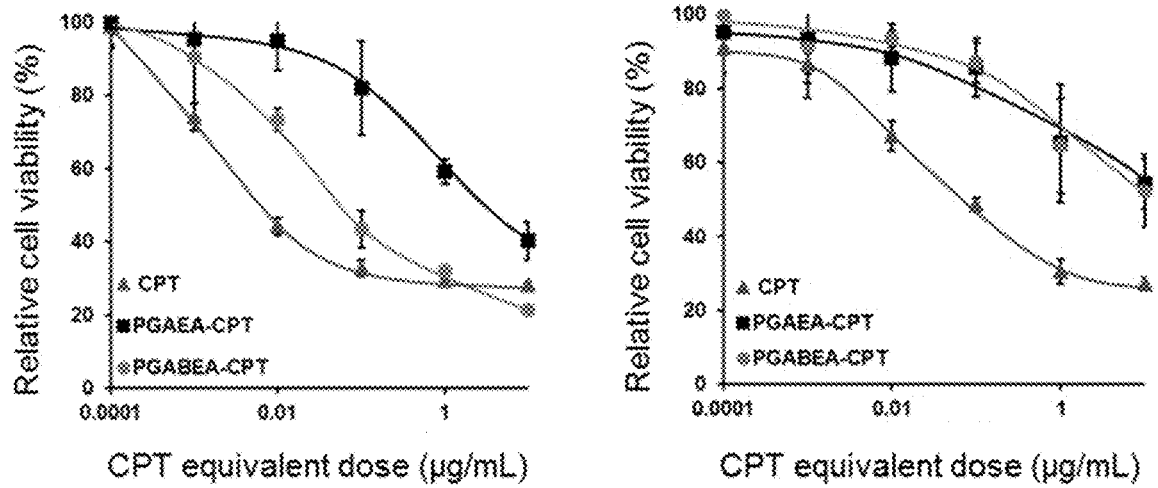
FIG. 7 shows the cytotoxicity assay curves of PGABEA-CPT, and PGAEA-CPT against γ-glutamyl transpeptidase-positive HepG2 cells and γ-glutamyl transpeptidase-negative NIH-3T3 cells in Application Example 1, wherein the figure on the left is cytotoxicity assay curves of PGABEA-CPT and PGAEA-CPT against γ-glutamyl transpeptidase-positive HepG2 cells; the figure on the right is cytotoxicity assay curves of PGABEA-CPT and PGAEA-CPT against γ-glutamyl transpeptidase-negative NIH-3T3 cells.

Comparative in vitro cytotoxicity test was performed for PGABEA-CPT with clinically used camptothecin small molecule CPT and PGAEA-CPT, which has a slow response to γ-glutamyl transpeptidase. The in vitro anti-tumor cell effects are shown in FIG. 7, respectively. It can be seen from the figure that PGABEA-CPT has similar cytotoxicity as CPT, which is significantly better than that of PGAEA-CPT with slow hydrolysis rate of γ-glutamyl transpeptidase. This result shows that PGABEA-CPT can be used as an anticancer drug.

(3) Plasma Clearance Experiment

Figure 8:
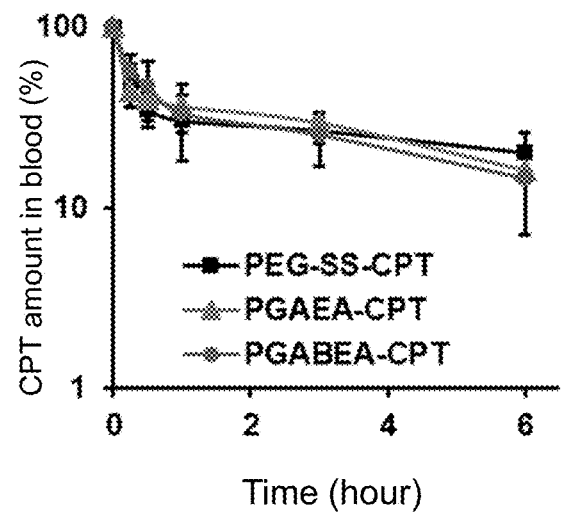
FIG. 8 shows the blood clearance kinetics of PGAEA-CPT, PGABEA-CPT or PEG-SS-CPT in mice of Application Example 1.

PGABEA-CPT and PEG-modified CPT (PEG-SS-CPT) were subjected to ICR mice plasma clearance experiment. ICR mice weighing about 20 g were randomly divided into 3 groups, and respectively injected with equivalent CPT amount of PGABEA-CPT, PGAEA-CPT and PEG-SS-CPT, blood from each group of mice was taken through the orbit at each set time point, and 50 µL of blood sample was taken to add into an equal volume of 0.1 mol/L NaOH solution, shake homogeneously. After blood collection of all time points was completed, the samples were placed in an oven at 37° C. overnight. Subsequently, 1 mL of acetonitrile was added to each centrifuge tube. The coagulated sample was broken by sonication, centrifuged to obtain the supernatant, and an equal amount of 0.1 M HCl solution was added, and was centrifuged again to obtain the supernatant. The CPT drug concentration was detected by HPLC and the working curve of the plasma clearance experiment was obtained. The experimental results are shown in FIG. 8. The results show that PGABEA-CPT and PEG-SS-CPT have similar in vivo circulation time. Therefore, PGABEA has similar long-circulation properties in vivo as PEG.

(4) Phagocytosis Assay for Cells Against Polymers PGABEA-CPT and PGAEA-CPT

PGABEA-CPT and PGAEA-CPT obtained in Example 3 were modified with fluorescent molecule Cy5 to obtain fluorescent molecule-labeled carrier molecules PGABEA$^{Cy5}$-CPT and PGAEA$^{Cy5}$-CPT; 150,000 of HepG2 cells or NIH-3T3 cells were plated in each well of a 12-well plate, after the cells adherent and cultured for 24 hours, add 5 µg/ml of PGABEA$^{Cy5}$-CPT and PGAEA$^{Cy5}$-CPT to each well. After incubating the cells in the cell incubator for a certain time, cells were subjected to PBS wash, trypsinization, centrifuge and PBS wash, and the resulting cells were tested for fluorescence intensity using a flow cytometer.

Similarly, seed 150,000 cells in a confocal dish. After the cells are completely attached to the well, add 5 µg/ml of PGABEA$^{Cy5}$-CPT and PGAEA$^{Cy5}$-CPT. After incubation for a specified time, wash the cells twice with PBS, lysotracker green was used to stain the lysosome, and Hoechst33342 was used stained the nucleus. Finally, the PGABEA$^{Cy5}$-CPT and PGAEA$^{Cy5}$-CPT invasion were observed under a laser confocal microscope.

Figure 9:
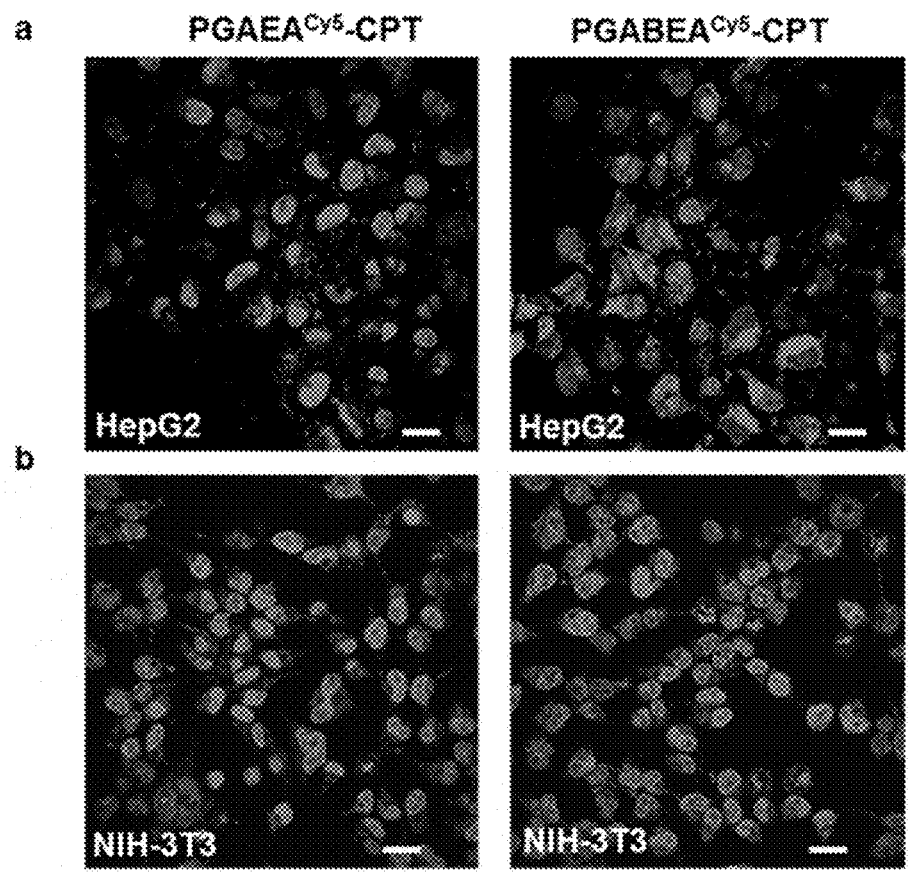
FIG. 9 shows laser confocal microscopy images of PGABEA$^{Cy5}$-CPT and PGAEA$^{Cy5}$-CPT in γ-glutamyl transpeptidase-positive HepG2 cells and γ-glutamyl transpeptidase-negative NIH-3T3 cells in Application Example 1, wherein a of the figure is the laser confocal microscopy image PGABEA$^{Cy5}$-CPT and PGAEA$^{Cy5}$-CPT in γ-glutamyl transpeptidase-positive HepG2 cells, b of the figure is the laser confocal microscopy image PGABEA$^{Cy5}$-CPT and PGAEA$^{Cy5}$-CPT in γ-glutamyl transpeptidase-negative NIH-3T3 cells.

The results are shown in FIG. 9. The experiment shows that the rate of PGABEA$^{Cy5}$-CPT molecules entering the cell is much higher than that of PGAEA$^{Cy5}$-CPT, and that PGABEA$^{Cy5}$-CPT is more positively charged after γ-glutamyl transpeptidase, so its rate of invasion also accelerated significantly.

(5) Tumor Penetration Assay

BALB/C nude mice were inoculated with 4×10$^6$ of HepG2 tumor cells under the armpit. After the tumor grew to about 200 mm$^3$, the PGABEA$^{Cy5}$-CPT and PGAEA$^{Cy5}$-CPT prepared in Example 5 were injected through the tail vein. After 6 hours, the tail vein was injected with FITC-labeled tomato agglutination to stain the blood vessels. Nude mice were sacrificed after 5 min. Tumor tissue was removed, embedded immediately for frozen section procedure, and tissues were sectioned for observation under a laser confocal microscope.

Figure 10:
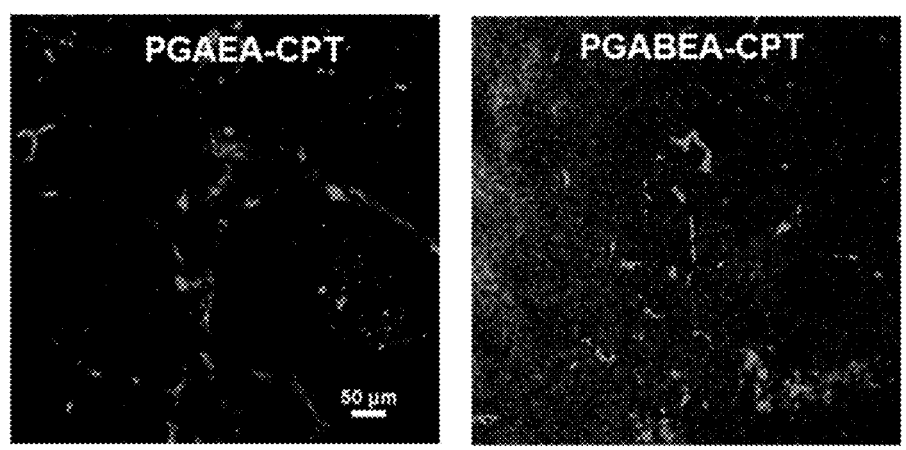
FIG. 10 shows comparative images of diffusion condition within the tumor of PGABEA$^{Cy5}$-CPT or PGAEA$^{Cy5}$-CPT in Application Example 1, wherein figure on the left is the diffusion image of PGAEA$^{Cy5}$-CPT in tumor tissue captured by laser confocal microscopy, figure on the right is the diffusion image of PGABEA$^{Cy5}$-CPT in tumor tissue captured by laser confocal microscopy.

The results are shown in FIG. 10. The experiment shows that, compared to the polymer PGAEA$^{Cy5}$-CPT which has a negative response to γ-glutamyl transpeptidase, the polymer PGABEA$^{Cy5}$-CPT which has a positive response to γ-glutamyl transpeptidase can penetrate deep into the tumor, while most of PGAEA$^{Cy5}$-CPT are stagnant around the blood vessels.

(6) Tumor Suppression Assay

Figure 11:
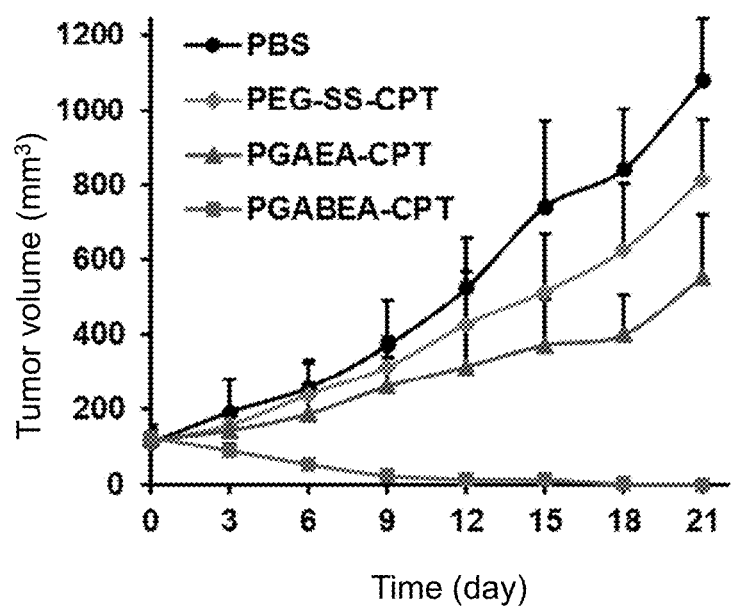
FIG. 11 shows tumor growth curve of the inhibition test of nude mice bearing HepG2 human liver cancer cells under treatment of drug PGABEA-CPT with control drug PGAEA-CPT and PEG-SS-CPT in Application Example 1.

To investigate the inhibitory effect of PGABEA-CPT on mice bearing tumor of HepG2 human hepatocellular carcinoma, BALB/C nude mice were inoculated with 4×10$^6$ HepG2 tumor cells under the armpit. After the tumors grew to about 100 mm$^3$, tail vein administration was initiated and administration was done for every two days. Four groups of nude mice, PGABEA-CPT, PGAEA-CPT, PEG-SS-CPT (CPT dose of 10 mg/kg) and the blank control group, respectively were administered for three times. The tumor volume was measured at each administration. After stopping the administration, observe for half a month to see if the tumor size has rebounded, and then the nude mice were sacrificed. After separating all the tumors, the average total wet weight of the tumors in each group is obtained. The results are shown in FIG. 11.

This result shows that compared with the PBS blank group, the tumor inhibition rate of the PGABEA-CPT group reaches 100%, while the tumor inhibition rates of the PEG-SS-CPT and PGAEA-CPT are only 20% and 48%, indicating that PGABEA, as a drug carrier, exhibits more significant anticancer activity than PEG as a drug carrier.

Figure 12:
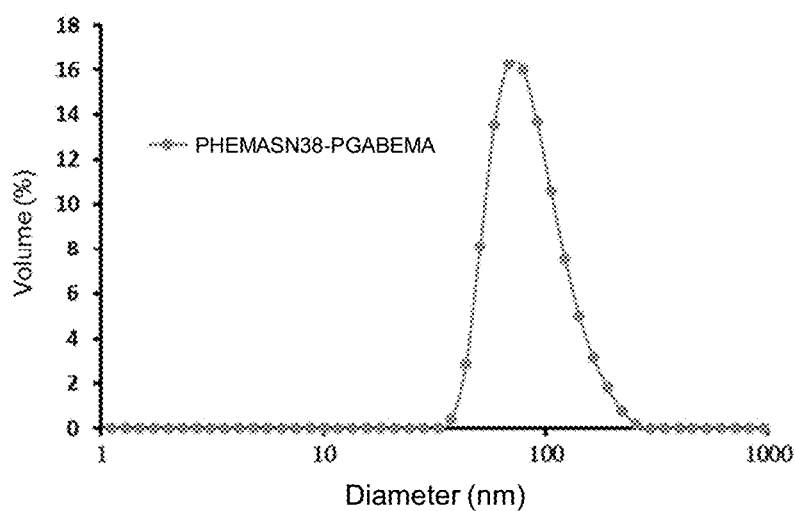
FIG. 12 shows the diameter sizes of PHEMASN38-PGABEMA micelles prepared in Application Example 2

Application Example 2: Application of PHEMASN38-PGABEMA Block Polymer as Anticancer Drug (1) Preparation of PHEMASN38-PGABEMA Micelles;

PHEMASN38-PGABEMA polymer (10 mg) was dissolved in 1 mL DMF, 5 mL of deionized water was added dropwise under rapid stirring, and the stirring was continued for 1 h. The micelle solution was placed in a dialysis bag with a molecular weight-cutoff of 3500 Da, and DMF was removed by dialysis to remove by deionized water to obtain a nanomicelle solution with a particle size of 100 nm (FIG. 12).

Figure 13:
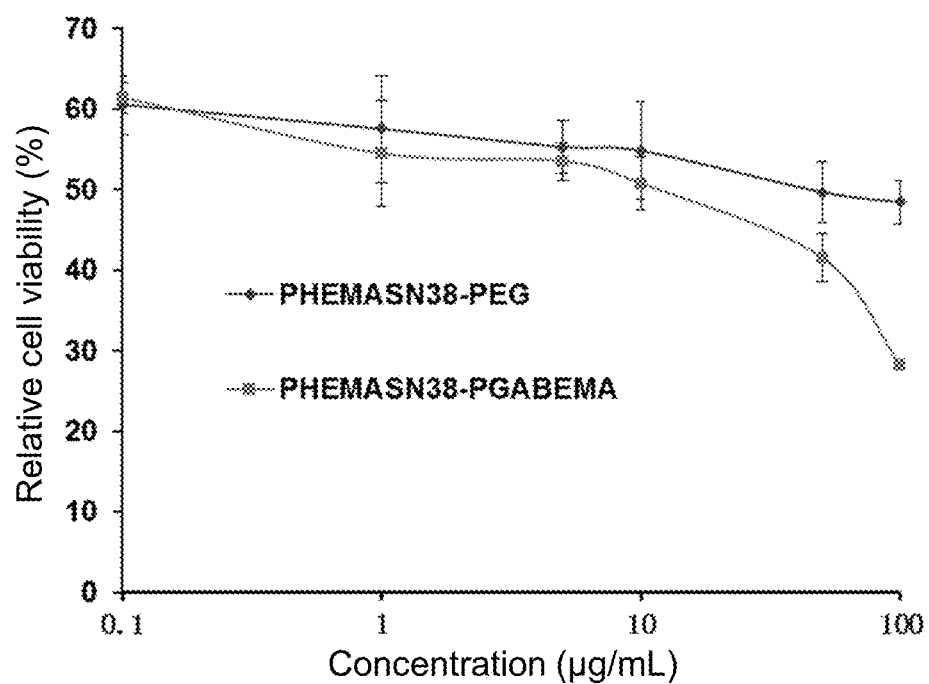
FIG. 13 shows the cytotoxic assay of PHEMASN38-PGABEMA, and control compound PHEMASN38-PEG in Application Example 2.

(2) PHEMASN38-PGABEMA Cytotoxicity Assay;

Comparative in vitro cytotoxicity assay for PHEMASN38-PGABEMA with PHEMASN38-PEG was performed, the in vitro anticancer effects are shown in FIG. 13, respectively. As can be seen from the figure, PHEMASN38-PGABEMA cytotoxicity is significantly better than PHEMASN38-PEG.

(3) PHEMASN38-PGABEMA Cell Endocytosis Test;

150,000 HepG2 cells were seeded in each well of a 12-well plate. After the cells were adhered to the wall for 24 hours, PHEMASN38-PGABEMA$^{RhoB}$ and PEG-PHEMASN38$^{RhoB}$ with the same fluorescence intensity were added to each well. After the cells were incubated in the cell incubator for a certain period of time, wash with PBS, trypsinize, centrifuge, and wash with PBS. Finally, the obtained cells were tested for intracellular fluorescence intensity by flow cytometry.

Similarly, seed 150,000 cells in a confocal dish. After the cells are completely attached, add PHEMASN38-PGABEMA$^{RhoB}$ and PEG-PHEMASN38$^{RhoB}$ with the same fluorescence intensity. After incubation for a specified time, wash the cells twice with PBS, and lyso-tracker green was used to stain the lysosome, Hoechst33342 was used to stain the nucleus, and finally the infiltration of PHEMASN38-PGABEMA$^{RhoB}$ and PEG-PHEMASN38$^{RhoB}$ was observed under the laser confocal microscope.

Figure 14:
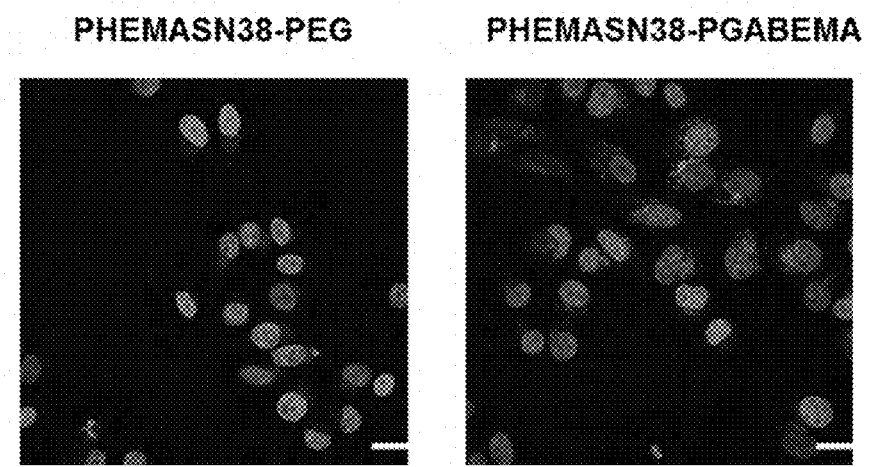
FIG. 14 shows the laser confocal microscopy image of the PHEMASN38-PGABEMA cells and control compound PHEMASN38-PEG cells in Application Example 2, wherein figure on the left is the laser confocal microscopy image of the PHEMASN38-PEG cells; figure on the right is the laser confocal microscopy image of the PHEMASN38-PGABEMA cells.

The results are shown in FIG. 14. This experiment shows that the rate of PHEMASN38-PGABEMA$^{RhoB}$ micelles entering the cell is much higher than that of PEG-PGABEMA$^{RhoB}$ micelles. This is because after the PGABEMA segment of PHEMASN38-PGABEMA$^{RhoB}$ is treated with γ-glutamyl transpeptidase and subjected to hydrolysis to generate amino groups, the micelles are positively charged, and hence the cell entry rate of the micelles is also significantly accelerated.

(4) Tumor Suppression Assay for PHEMASN38-PGABEMA Micelles

To investigate the inhibitory effect of PHEMASN38-PGABEMA on mice bearing tumor of HepG2 human hepatocellular carcinoma, BALB/C nude mice were inoculated with 4×10$^6$ HepG2 tumor cells under the armpit. After the tumor grew to about 450 mm$^3$, tail vein administration was initiated, administration was done in every two days, and a total administration of three times was performed.

Figure 15:
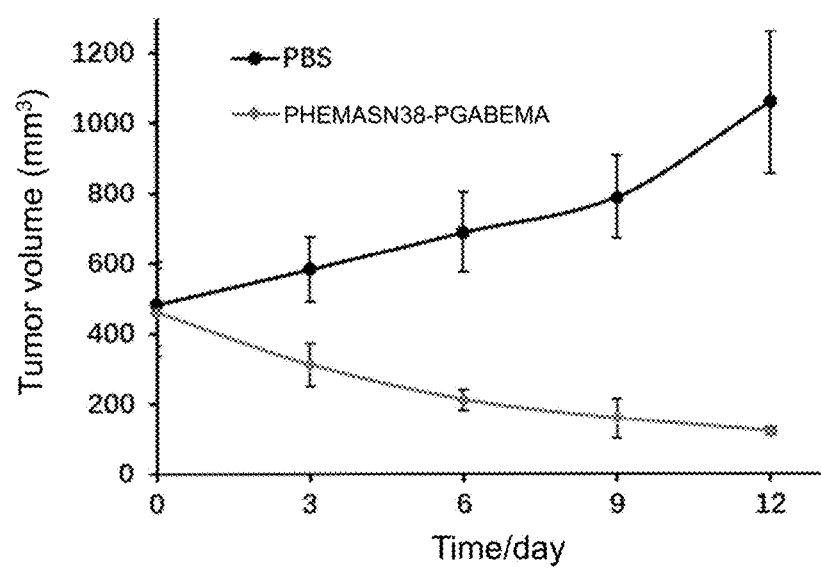
FIG. 15 shows the HepG2 tumor growth inhibition curves under PHEMASN38-PGABEMA in Application Example 2.

The results are shown in FIG. 15. Although the tumor of the nude mice had grown to 450 mm$^3$ during the first administration, after three times of treatment with PHEMASN38-PGABEMA, the tumor size of the mice became significantly reduced, and there was no obvious rebound after the administration is stopped.

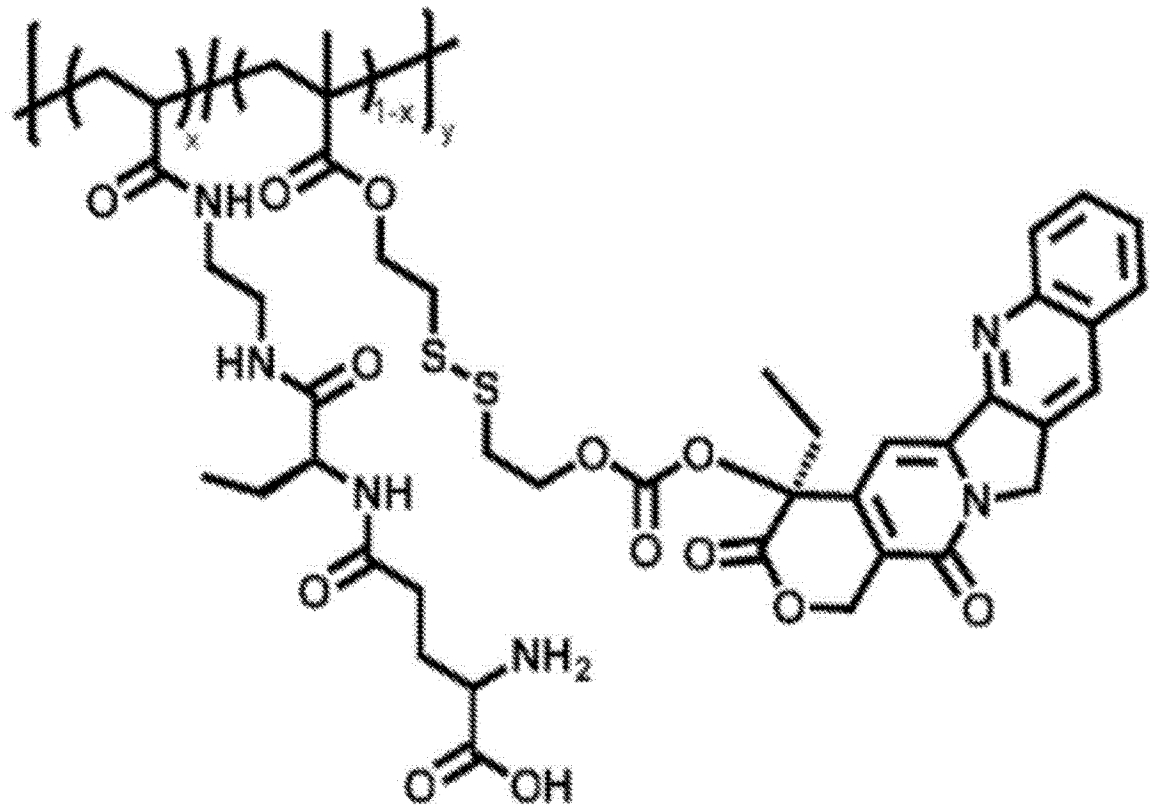

What is claimed is:

1. A drug carrier having a structure represented by Formula (IIIa) or Formula (IVa):

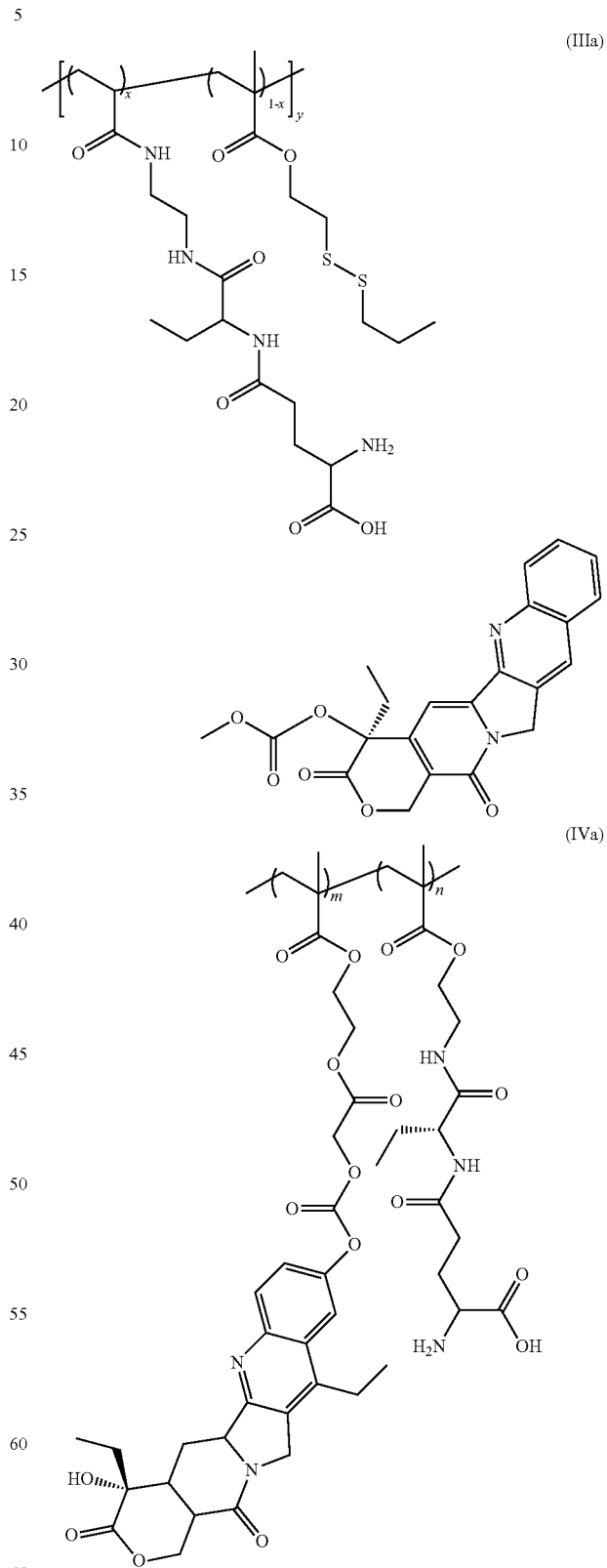

wherein, x=0.01-0.99, y=3-300, m=3-300, and n=3-300.

2. A method for preparing the drug carrier according to claim 1, comprising:

performing a random copolymerization or a block copolymerization between a monomer containing a γ-glutamyl transpeptidase responsive element and a monomer of a loaded drug.

\* \* \* \* \*

UNITED STATES PATENT AND TRADEMARK OFFICE
CERTIFICATE OF CORRECTION

PATENT NO. : 11,534,435 B2  
APPLICATION NO. : 17/662351  
DATED : December 27, 2022  
INVENTOR(S) : Youqing Shen et al.

Page 1 of 2

It is certified that error appears in the above-identified patent and that said Letters Patent is hereby corrected as shown below:

In the Specification

Column 6, Line 25, and Claim 1, Column 20, Line 38, Formula (IVa) should appear as follows:

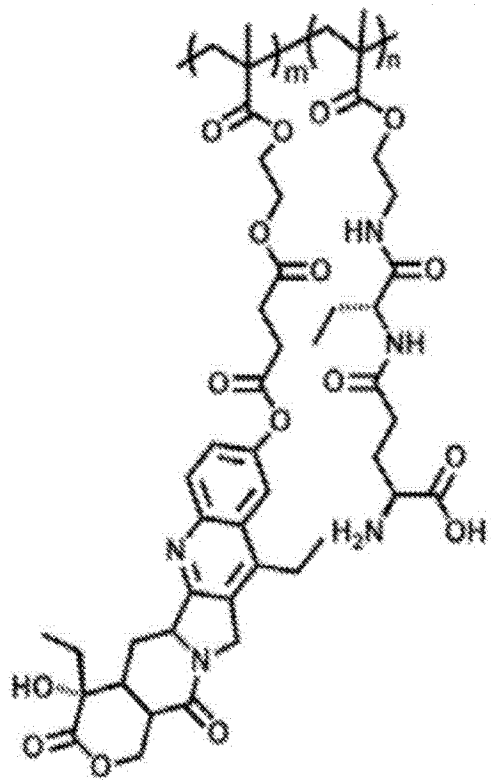

Column 9-10, Line 25, the portion of the synthetic scheme reading "$H_2O/CHCl_2$" should read --$H_2O/CHCl_3$-- and the portion of the formula reading "$NH_3^+CF_2COO^-$" should read --$NH_3^+CF_3COO^-$--

Signed and Sealed this  
Fourteenth Day of March, 2023

*Katherine Kelly Vidal*

Katherine Kelly Vidal  
*Director of the United States Patent and Trademark Office*

CERTIFICATE OF CORRECTION (continued)

In the Claims

Claim 1, Column 20, Line 5, Formula (IIIa)'s structure should appear as follows: